United States Patent [19]
Brown, Jr.

[11] Patent Number: 4,691,712
[45] Date of Patent: * Sep. 8, 1987

[54] DEVICE FOR DETECTING, MEASURING, AND RECORDING BODY THERMAL EMISSIVITY

[75] Inventor: George T. Brown, Jr., Dayton, Ohio

[73] Assignee: American Thermometer Co., Inc., Dayton, Ohio

[*] Notice: The portion of the term of this patent subsequent to Jun. 25, 2002 has been disclaimed.

[21] Appl. No.: 747,017

[22] Filed: Jun. 20, 1985

Related U.S. Application Data

[63] Continuation of Ser. No. 515,503, Jul. 20, 1983, Pat. No. 4,524,779.

[51] Int. Cl.⁴ ............................................. G03B 29/00
[52] U.S. Cl. ...................................... 125/736; 354/81
[58] Field of Search .................... 128/736; 354/18, 81, 354/293

[56] References Cited

U.S. PATENT DOCUMENTS

| | | | |
|---|---|---|---|
| 3,335,716 | 8/1967 | Alt et al. | 128/736 X |
| 4,101,696 | 7/1978 | Jennen et al. | 128/736 X |
| 4,135,497 | 1/1979 | Meyers et al. | 128/736 |
| 4,310,003 | 1/1982 | Schlager | 128/736 |
| 4,327,743 | 5/1982 | Katz | 128/736 |
| 4,524,778 | 6/1985 | Brown, Jr. et al. | 128/736 |
| 4,524,779 | 6/1985 | Brown, Jr. | 128/736 |

FOREIGN PATENT DOCUMENTS 2060879 5/1981 United Kingdom ................ 128/736

Primary Examiner—William E. Kamm
Assistant Examiner—Angela D. Sykes
Attorney, Agent, or Firm—Jacox & Meckstroth

[57] ABSTRACT

A device for detecting thermal differentials emanating from a radiant source by transforming such differentials to visible representations that can be photographically recorded for subsequent diagnostical and analytical study. The device includes a light transmitting housing having one end supporting a resilient frame with a flexible thermally responsive screen an opposite end supporting a camera. The device is especially useful in the early detection of cancer or of other contralateral heat differentials in the body due to various abnormal or disease conditions or to monitor chemotherapy or progress of surgical recovery.

19 Claims, 10 Drawing Figures

U.S. Patent    Sep. 8, 1987    Sheet 1 of 2    4,691,712
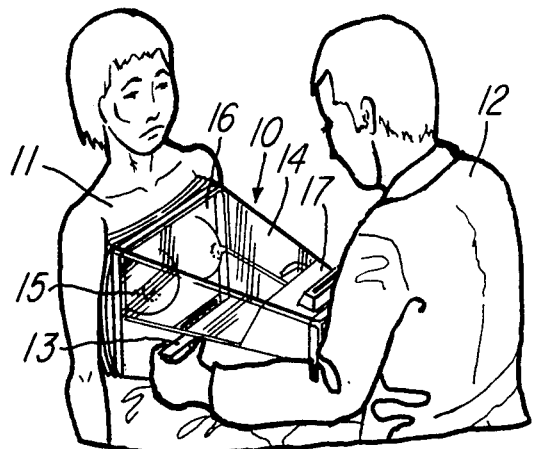
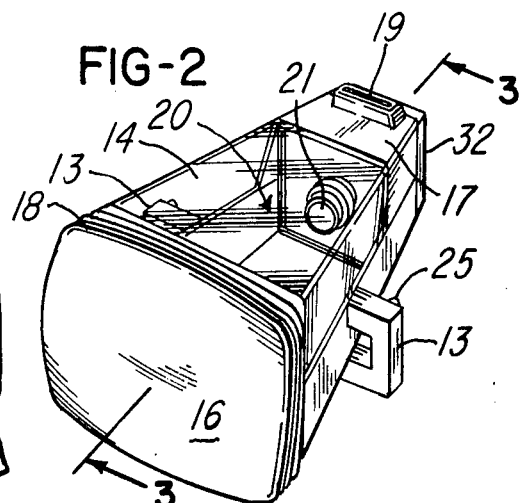
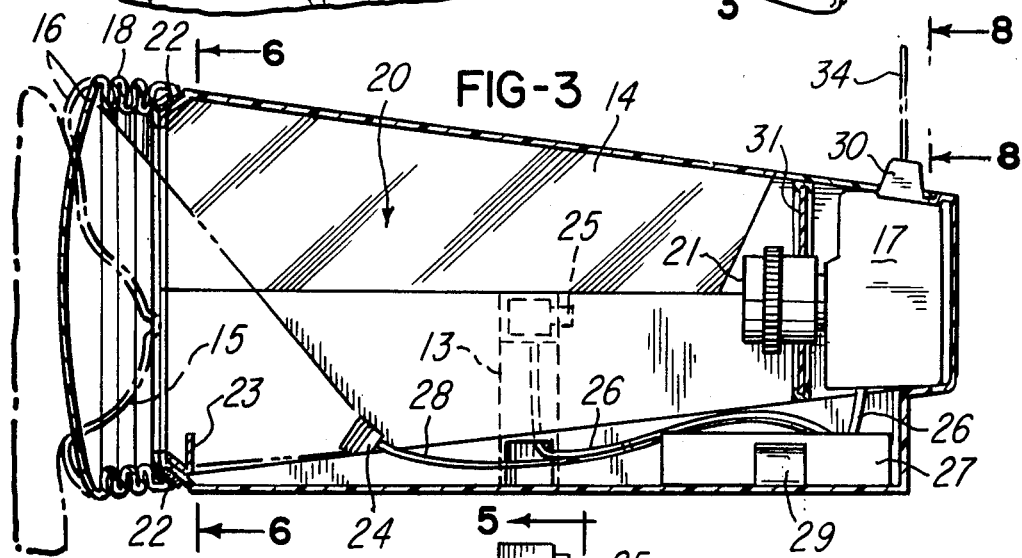
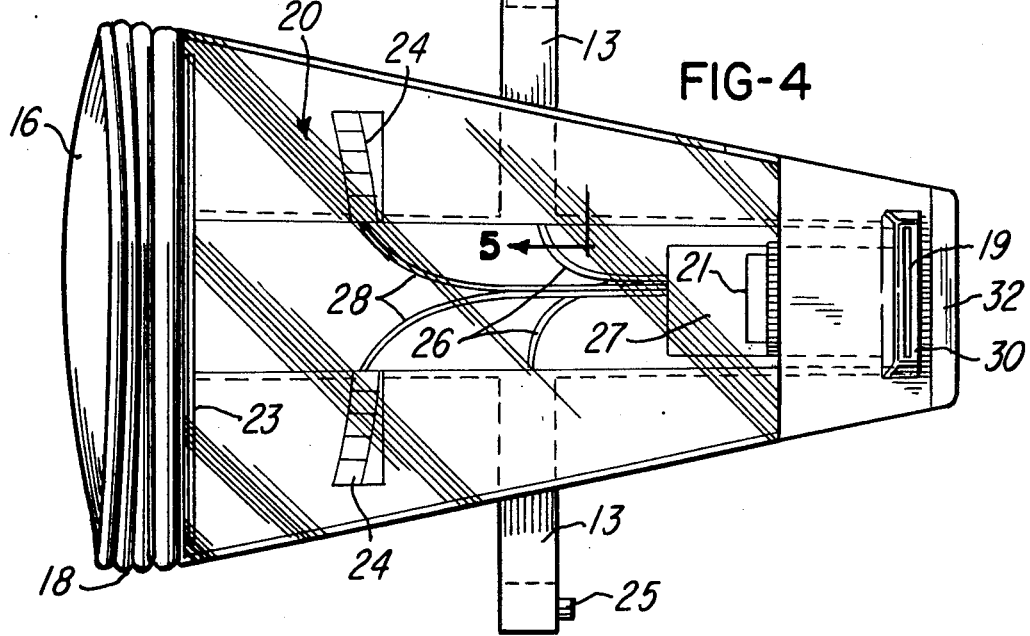

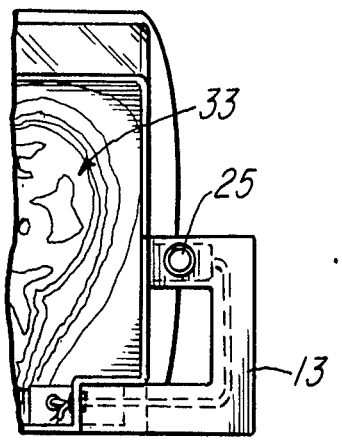
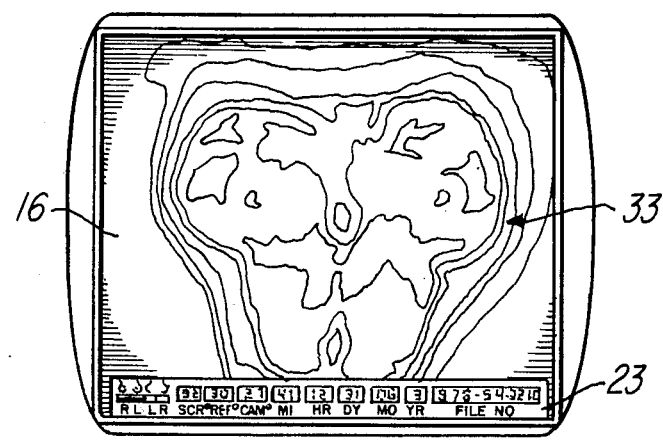
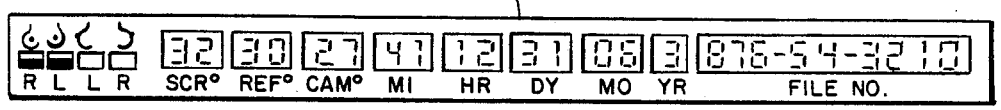
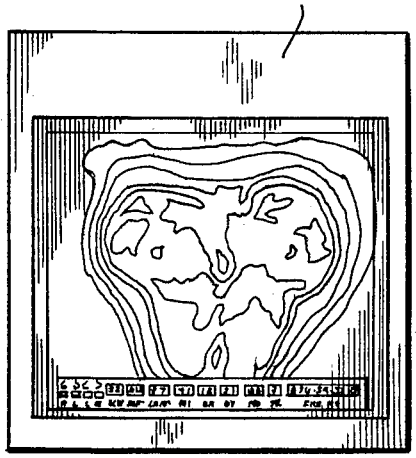
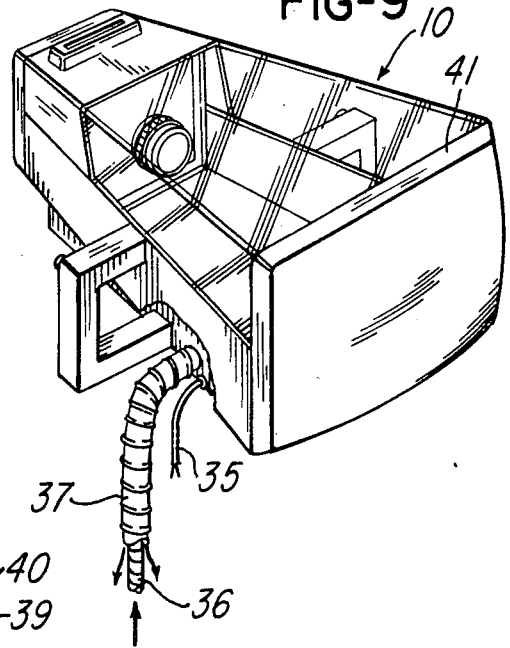
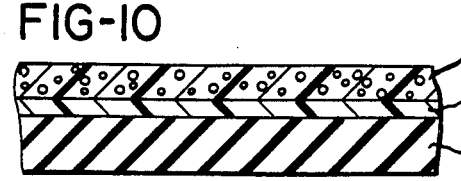

DEVICE FOR DETECTING, MEASURING, AND RECORDING BODY THERMAL EMISSIVITY

RELATED APPLICATION

This application is a continuation of application Ser. No. 515,503, filed July 20, 1983, now issued as U.S. Pat. No. 4,524,779.

BACKGROUND OF THE INVENTION

1. Field of the Invention

The present invention relates generally to a device for detecting thermal differentials emanating from a body and for transforming such differentials to a visible representation for thermographic recording. More particularly, the invention relates to a combination of an elastomeric film containing temperature responsive cholesteric liquid crystals to locate and to convert surface areas of temperature gradients to color patterns and an imaging system for photographing such patterns.

2. Description of the Prior Art

Medical literature is increasingly demonstrating how thermal sensing devices and materials can aid in the diagnosis of disorders when correlated with an individual's clinical history, physical examination and other laboratory tests and in the study of physiological reactions to pharmodynamic substances such as immunological, hormonal and vasomotor drugs. The field of study involving the use of thermal sensing devices and materials, or thermography, may be defined as a process for detecting abnormal or diseased underlying conditions of an organism which produce temperature changes and for transforming these resulting thermal differentials emanating from such disorders or lesions to a visible display for photographic recording and analysis.

Early work, which was conducted to determine a methodology whereby elevated or so-called "hot areas", created by an infusion of an extraordinary number of blood vessels, may be indicative of an underlying disorder such as a neoplast, involved the remote sensing of the infrared radiation emitted from a scanned area. However, the sensing equipment developed to detect the emitted radiation produced thermographic outputs that erroneously indicated positive readings. Because of the frequency of such false readings, the lack of agreement as to the results obtained made the procedure unacceptable. Furthermore, such electronic infrared sensing equipment is very expensive and requires the use of skilled personnel.

Independent of the work in the area of electronic infrared thermography since 1968 there has been a substantial effort in laboratories throughout the world in developing display devices and temperature sensors using liquid crystals. These compounds, which conventionally are divided into three classes, namely, smetic, nematic, and cholesteric, possess one or more mesomorphic phases, intermediate between their solid crystal form and their isotropic form. In response to subtle temperature changes the colorless isotropic form of cholesteric liquid crystals, due to their unique molecular structure, undergoes an optical transformation as it passes through the highly colored mesomorphic phase.

As an alternative to electronic infrared thermography researchers directed cholesteric thermotropism to the problem of visually viewing invisible radiation emitted from an object which falls within the infrared portion of the electromagnetic spectrum. Early disclosures such as contained in U.S. Pat. No. 3,533,399 revealed a procedure whereby a first layer most commonly comprising a black pigment and a second layer of cholesteric substances were applied to the skin area under investigation to produce visible thermal patterns that could be photographed. The impracticality of the time consuming procedure for mass screening and routine examination, the nonreuseability of materials, the uneasiness of patients negatived acceptance of the procedure.

In order to overcome the disadvantages inherent in the procedure of coating body areas with temperature responsive materials and their subsequent removal, nonuniformity of coatings, nonrecovery of materials, thermometric devices comprising liquid crystal materials that scan a surface area to produce thermograms containing information pertaining to temperature variations over the scanned areas were disclosed. U.S. Pat. No. 3,847,139 is typical of such disclosures in which body contour garments, such as brassieres, incorporating temperature responsive substances produce thermal patterns that are observed and photographically recorded for comparative analysis. Due to differences of sizes and shapes of women's breasts, such garments are not satisfactory because they lack the conformability necessary to uniformally contact all of the scanned areas being investigated.

Disclosed as a process (particularly for the detection of mammary anomalies) that overcomes the inherent disadvantages of coating body areas with thermosensitive materials, or the use of flexible supports disposed against the surface under examination, or the utilization of supports called "thermosensitive pellicles with liquid crystals", U.S. Pat. No. 4,060,654 teaches the use of a composite lamellar pellicle for producing photographable thermographic patterns by using liquid crystal materials applied to an inner sheet and sandwiched between two outer sheets which are enframed to preserve the planar shape. By using a temperature responsive series of pellicles containing different admixtures of liquid crystal materials, the practitioner can determine the thermal topography of a body regardless of the ambient temperature. However, because the pellicles are mounted in rigid rectangular frames, the device is conformability restricted in that it cannot be used on curved surface areas. Furthermore, lamellar pellicle thermography and the interpretation of thermograms is limited to clinical research facilities, hospitals, and doctors offices; being unsuited for direct use by the patient in her home.

In order to overcome the conformability limitations of thermoresponsive fabric brassieres and lamellar pellicles, a brassiere-like apparatus, as disclosed in U.S. Pat. No. 4,135,497, provides liquid crystals interposed between flexible sheets to form a composite film. Conformance of the film to the contours of the body is attained by evacuation of air between the film secured in place by means of a pair of elastic straps encircling the women's chest and the body surface. The heat emitted by tissues of the various regions are transformed by the film into color patterns or thermograms which may be photographically recorded. However, the excessive time consuming special techniques to ensure body conformity tends to obviate the apparatus as a practical procedure for mass screenings and routine examinations, apparatus bulk and complexity preclude its use to the more sophisticated medical facilities, and narrow thermoresponsive range composite film limit the application of a film to a particular tissue region.

SUMMARY OF THE INVENTION

The present invention provides a device for detecting thermal differentials emanating from a radiant source by transforming such differentials to visible representations that can be photographically recorded for subsequent diagnostical and analytical study. The device is generally frustum-of-a-pyramid-shape, relatively pressure tight, partially transparent, two handle-grip enclosure having a contour-conformable, thermoresponsive screen and a specially designed photographic system to record resultant thermochromatic patterns. A practitioner grasps the handle-grips and places the temperature sensitive end into contact with the body area under study, for example, the breasts of a female, and a flow of air through the enclosure helps conform the screen and controls its temperature. The resulting thermogram that appears on the thermoresponsive screen is observed by the practitioner by peering through the top transparent wall of the device. By pressing a button located in the handle-grips the photographic system is activated and the thermogram is recorded. The ability to view a body area before photographic recordation enables the practitioner to scan the general area under study to select the most meaningful thermograms for recording.

It is therefore an object of the present invention to provide a device for detecting and measuring body thermal emissivity which is capable of providing a photographic record of high resolution thermographic display of a small temperature change occurring at any point within a relatively broad temperature range over a various portion of a body.

It is a further object of the invention to provide a device for detecting, measuring, and recording body thermal emissivity for use in the early detection of cancer or of other contralateral heat differentials in the body due to various abnormal or disease conditions or to monitor chemotherapy or progress of surgical recovery.

Still another object of the invention is to provide a device for detecting, measuring, and recording body thermal emissivity which is so designed and constructed that such device may be easily and conveniently used for mass screenings and routine examinations by persons with limited special training or skills and without complicated or expensive equipment or support apparatus or carefully controlled environmental conditions.

Yet another object of the invention is to provide a sanitary method whereby thermographic data can be conveniently and permanently recorded for regular periodic comparative thermal analysis extending over long periods of time at low cost.

Achievement of the above and other objects and advantages which will be apparent from a reading of the following disclosure and overcoming of shortcomings and disadvantages of prior art devices have preceded in the case of the present invention from the discovery by the instant inventor that records of good resolution of precise and readily distinguishable chromatic changes in response to relatively small temperature changes over a relatively broad temperature range may be achieved by the use of conformably designed and specially constructed reuseable liquid crystalline systems affixed to a suitable thin, elastic substrate to be held in contact with an area of surface to be investigated.

BRIEF DESCRIPTION OF THE DRAWINGS

For a further understanding of the nature of objects of the invention, reference should be had to the detailed description of the exemplary embodiments taken in connection with the appended drawings in which:

FIG. 1 is a perspective view of a device constructed in accordance with this invention showing a practitioner at the back or practitioner end of the device holding the front or patient end of the device against the upper torso of a female by means of a pair of handle-grips and viewing the area under examination through the transparent window that forms a portion of the top side of the device.

FIG. 2 is a front perspective view of the device shown in FIG. 1 to particularly illustrate a thermoresponsive screen, the pair of handle-grips, and a camera for processing color film.

FIG. 3 is a cross sectional view of the device taken along the line 3—3 of FIG. 2 particularly illustrating a portion of a photographic system and the normally at-rest thermoresponsive screen affixed to bellows as depicted with unbroken lines. FIG. 3 also illustrates a female breast which shapes the thermoresponsive acreen as depicted with the broken lines.

FIG. 4 is a top planar view of the device in accordance with this invention particularly illustrating a pair of internally housed flash lamps of the photographic system, right and left handle-grips with a pair of switches to activate the photographic process, and the thermoresponsive screen with a body fitting bellows affixed to the support housing of the device.

FIG. 5 is a fragmentary cross sectional view of the device looking forward along with line 5—5 of FIG. 4 particularly illustrating a thermogram displayed on the thermoresponsive screen and one of the handle-grips with a trigger.

FIG. 6 is an elevational view of the device looking forward along the line 6—6 of FIG. 3 particularly illustrating a thermogram displayed on the thermoresponsive screen and a data display showing patient pertaining information.

FIG. 7 is an enlarged elevational view of the patient information strip illustrated in FIG. 6.

FIG. 8 simulates an actual simultaneous "instant-print" photograph of the thermogram and data display illustrated in FIG. 6.

FIG. 9 is a perspective view of an embodiment of a device in accordance with the invention having a thermoresponsive screen affixed to the front or patient end of the device and a temperature and humidity controlled recirculating air supply.

FIG. 10 is a fragmentary cross sectional view of the thermoresponsive screen of this invention.

DESCRIPTION OF THE PREFERRED EMBODIMENTS

Referring to FIG. 1, a thermal emissivity device 10 of this invention is held against the upper torso of a patient 11 by a practitioner 12 by means of a pair of handle-grips 13 affixed to device 10. A portion of the top and side walls 14 of device 10, which is generally frustum-of-a-pyramid shaped, is constructed with transparent material in order that the interior of device 10 can be illuminated with ambient light. Ambient illumination of the interior of device 10 allows practitioner 12 to observe the pair of breasts 15 shown on a thermoresponsive screen 16 which comprises an encapsulated liquid crystal thermoresponsive material system affixed to an elastomeric substrate, hereinafter described in greater detail. The normally concave configuration of thermoresponsive screen 16 is shaped by the pair of breasts 15 making intimate thermal contact with the thermoresponsive material system.

Heat differentials which may be created by an infusion of an extraordinary number of involved blood vessels into any of the breast area are transformed by the thermoresponsive material system into a color display discernible by practitioner 12. After viewing the display, if practitioner 12 decides that a permanent record is required, provided in the pair of handle-grips 13 is a triggering mechanism 25, particularly shown in FIGS. 3 and 4, that activates an internally housed photographic system. Referring to FIGS. 1-4, located rearwardly within device 10 is camera 17 for recording color displays of thermoresponsive screen 16. Preferably camera 17, sold under the trademark Champ Kodamatic by Eastman Kodak Co., Rochester, N.Y., is inverted from the normally used position so that the color print is now automatically ejected upwards through exit slot 19 on the top side of device 10. In addition to cameras that produce color prints, cameras that produce images on film or images on video screens can also be used.

Optical chamber 20, which is a portion of a device 10 defined by the four device walls, the sensitive side of thermoresponsive screen 16, and the lens side of camera 17, is relatively air tight in order to eliminate deleterious materials including film processing chemicals and medical vapors. Rearwardly housed within optical chamber 20 for sharper focusing is an accessory lens 21 axially located approximately 18 inches from thermoresponsive screen 16 and capable of covering an active screen area of about 9 inches by 13 inches. Thermoresponsive screen 16 is affixed to conformable rim 18 by means of an adhesive, flexible clamp, elastic band, or any combination thereof and conformable rim 18 is held in place onto optical chamber 20 by means of a snap or a high friction joint 22 which allows easy interchanging of various conformable rims. The body fitting conformable rim 18 may be constructed from elastomeric, plastic, or paper materials suitable for accordian folds or from closed cell compressible foam. As previously indicated when device 10 is pressed against the upper torso of a patient 11, thermoresponsive screen 16 conforms to the shape of breasts 15 (shown by the broken lines in FIG. 3) simultaneously causing portions of thermoresponsive screen 16 not in contact to breasts 15 to bulge outwardly of device 10.

Referring to FIGS. 3 and 4, housed in optical chamber 20 are: rearwardly and downwardly of thermoresponsive screen 16 is data strip 23 which appears in the field of view of lens 21; rearwardly of data strip 23 and on the floor of optical chamber 20 are two commercially available illumination assemblies 24 each having a flash lamp and front surface diffuser lens; rearwardly of illumination assemblies 24 is power supply 27 and cover clip 29 to secure power supply 27 to device 10; and electrical cables 26 interconnecting the triggering mechanism 25 and camera 17 and power supply 27, and high voltage wires 28 interconnecting illumination assembly 24 and power supply 27. Forming a rearward vertical wall of optical chamber 20 is camera adjustable mounting plate 31 which is integrally part of and is used to axially align camera 17 with thermoresponsive screen 16. Except for lens 21 camera 17 is located outside optical chamber 20 in a compartment formed by the camera adjustable mounting plate 31, back plate 32, and the four outer walls of device 10. After an exposure is processed, a photographic record 34 is ejected through film exit slot 19 in film pack door 30 of camera 17.

Referring to FIGS. 5-8, if practitioner 12 decides that a color pattern 33 appearing on thermoresponsive screen 16 should be photographically recorded, while holding handle-grips 13, he merely depresses button 25. However, before activating the photographic process, practitioner 12 enters patient pertaining information into data strip display 23 by means of a conventional keyboard which may be located at back plate 32 or remote from device 10. Typical keyboard entered information comprises a file no. (social security number), the time a color pattern was photographed (minute, hour, day, month, and year), the temperature of optical chamber 20 (cam°), patient's body temperatuure determined by a reference thermometer (ref°), a reference temperature of thermoresponsive screen 16 (scr°), and a indication mark that the photograph is a full frontal view of the right (r) and left (l) breast or a side view of the right (r) or left (l) breast.

Referring to FIG. 9, a thermoresponsive plate 41 comprising a flexible rim and a thermoresponsive screen is held in place onto device 10 (as shown in FIG. 3) by means of a snap or a friction joint which allows easy interchanging of a series of thermoresponsive plates that range from 26° C. to 38° C. Preparation of the thermoresponsive plates 41 containing encapsulated liquid crystalline esters 2-50 microns in diameter are formed and composed as described in application Ser. No. 404,506, filed Aug. 2, 1982. Also in this embodiment of the invention, temperature and humidity controlled air is supplied on generally continuous basis to the internal portion of device 10 through tube 36 and is exhausted through tube 37 to aid in controlling the temperature of the air within the chamber 20. A cable 35 supplies power to device 10 from an external source in lieu of battery power supply 27. In order to maintain thermoresponsive screen 16 sanitary and free of deleterious external substances, a 4-7 mil plastic film, preferably polyester, is placed over thermoresponsive plate 41 and is held in place by a flexible rim slightly larger than the rim affixed to device 10.

Referring to FIG. 10, thermoresponsive screen 16 of this invention comprises a 4-8 mil elastomeric substrate 38, for example, a polyurethane or a polyisoprene rubber sheath such as can be obtained from the Hygenic Corporation, Akron, Ohio, onto which is affixed about a 2 mil black layer 39 and a 4-6 mil layer 40 of encapsulated liquid crystals. Acrylic rubber added to the admixtures of layers 39 and 40 increases the elastic properties of these layers and make them more compatible with elastomeric substrate 38. Preparation of the admixtures of layers 39 and 40 are described in U.S. application Ser. No. 509,933, filed July 1, 1983 entitled SKIN TEMPERATURE INDICATING AND RECORDING DEVICE.

While the within invention has been described in connection with certain preferred embodiments thereof, it is to be understood that the foregoing particularization and detail have been for the purposes of description and illustration only and do not in any way limit the scope of the invention as it is more precisely defined by the claims.

What is claimed is:

1. A device for detecting and recording the thermal emissivity of a human body, comprising a housing having opposite forward and rearward end portions, a flexible thermal responsive screen adapted to conform to the contour of the body and having a coating of liquid crystals effective to transform thermal differentials emanating from the body to visible color patterns, a resilient frame mounted on said forward end portion of said housing and supporting said flexible screen, said frame being conformable to the contour of the body in response to pressure of the body against said frame, camera means for recording the image of the patterns, means mounted on said rearward end portion of said housing for supporting said camera means, said housing cooperating with said screen and frame to define a chamber, and means for applying a fluid pressure against said flexible screen and cooperating with said resilient frame to conform said screen to the contour of the body.

2. A device as defined in claim 1 wherein said housing has tapering walls with said forward end portion being larger than said rearward end portion, and means for removably connecting said resilient frame to said forward end portion of said housing.

3. A device as defined in claim 2 wherein said housing has a frusto-pyramid configuration.

4. A device as defined in claim 1 wherein said housing comprises light transmitting opposite side wall portions connected by a light transmitting top wall portion for transmitting light surrounding said housing into said chamber and onto said screen and for viewing the patterns.

5. A device as defined in claim 1 and including handle means projecting outwardly from said housing for manually gripping and supporting said device with said screen in a generally vertically position.

6. A device as defined in claim 1 wherein said screen and said frame are generally rectangular, and means for releasably attaching said resilient frame to said housing.

7. A device as defined in claim 1 and including means for releasably attaching said resilient frame to said housing to provide for conveniently interchanging said screen with another screen having different coatings of liquid crystals corresponding to different temperature ranges.

8. A device as defined in claim 7 wherein said means for releasably attaching said frame comprise a friction-fit coupling forming a generally air-tight seal.

9. A device as defined in claim 1 wherein said resilient frame comprises a flexible material forming a resilient wall.

10. A device as defined in claim 1 wherein said resilient frame comprises a flexible wall having a generally uniform thickness.

11. A device for detecting and recording the thermal emissivity of a human body, comprising a flexible thermal responsive screen adapted to conform to the contour of the body and having a coating of liquid crystals effective to transform thermal differentials emanating from the body to visible color patterns, a resilient frame supporting said flexible screen, said frame being conformable to the contour of the body in response to pressure of the body against said frame, camera means for recording the image of the patterns, means connected to said frame and supporting said camera means in predetermined spaced relation to said screen, and means for applying a fluid pressure against said flexible screen and cooperating with said resilient frame to conform said screen to the contour of the body.

12. A device as defined in claim 11 wherein said means for applying fluid pressure against said screen comprise means for applying air pressure against said screen and within said resilient frame.

13. A device as defined in claim 11 wherein said means connected to said frame and supporting said camera comprise a housing having light transmitting opposite side wall portions connected by a light transmitting top wall portion for transmitting light surrounding said housing into said chamber and onto said screen and for viewing the patterns.

14. A device as defined in claim 13 wherein said screen and said resilient frame are generally rectangular.

15. A device as defined in claim 13 and including means for releasably attaching said resilient frame to said housing to provide for conveniently interchanging said screen with another screen having different coatings of liquid crystals corresponding to different temperature ranges.

16. A device as defined in claim 15 wherein said means for releasably attaching said frame comprise a friction-fit coupling forming a generally air-tight seal.

17. A device as defined in claim 11 wherein said resilient frame comprises a flexible material forming a resilient wall.

18. A device as defined in claim 11 wherein said resilient frame comprises a flexible wall having a generally uniform thickness.

19. A device for detecting and recording the thermal emissivity of a human body, comprising a housing having opposite forward and rearward end portions connected by converging light transmitting wall portions, a flexible thermal responsive screen adapted to conforrm to the contour of the body and having a coating of liquid crystals effective to transform thermal differentials emanating from the body to visible color patterns, a resilient frame mounted on said forward end portion of said housing and supporting said flexible screen, said frame being conformable to the contour of the body in response to pressure of the body against said frame, camera means for recording the image of the patterns, and means mounted on said rearward end portion of said housing for supporting said camera means.

* * * * *